United States Patent [19]

Kelton et al.

[11] Patent Number: 4,938,927
[45] Date of Patent: Jul. 3, 1990

[54] ROTARY FLUID MANIPULATOR

[75] Inventors: Arden A. Kelton, Westminster; Michael L. Bell, Corona; Roy A. Chung, Fountain Valley, all of Calif.

[73] Assignee: Environmental Diagnostics, Inc., Burlington, N.C.

[21] Appl. No.: 356,581

[22] Filed: May 22, 1989

Related U.S. Application Data

[63] Continuation of Ser. No. 338,123, Jan. 8, 1982, abandoned.

[51] Int. Cl.⁵ .................. G01N 35/00; G01N 33/558; C12N 11/12
[52] U.S. Cl. .......................... 422/64; 422/56; 422/72; 435/179; 435/291; 435/805; 436/514; 436/45; 436/809
[58] Field of Search ................. 422/72, 71, 70, 69, 422/57, 56, 64; 436/514, 515, 807, 808, 809, 44, 45; 435/179, 291, 805

[56] References Cited

U.S. PATENT DOCUMENTS

| | | | |
|---|---|---|---|
| 3,723,064 | 3/1973 | Liotta | 422/56 |
| 3,744,975 | 7/1973 | Mailen | 422/72 |
| 4,087,326 | 5/1978 | Kereluk | 195/103.5 R |
| 4,087,332 | 5/1978 | Hansen | 195/103.5 R |
| 4,123,173 | 10/1978 | Bullock et al. | 356/246 |
| 4,133,639 | 1/1979 | Harte | 422/71 |
| 4,225,558 | 9/1980 | Peterson et al. | 422/72 |
| 4,233,029 | 11/1980 | Columbus | 422/55 |
| 4,237,234 | 12/1980 | Meunier | 435/301 |
| 4,244,916 | 1/1981 | Guigan | 422/72 |
| 4,270,921 | 6/1981 | Graas | 422/72 |
| 4,279,862 | 7/1981 | Bretaudiere et al. | 422/72 |
| 4,298,345 | 11/1981 | Sodickson et al. | 422/56 |
| 4,301,139 | 11/1981 | Feingers et al. | 436/808 |
| 4,323,536 | 4/1982 | Columbus | 422/56 |
| 4,338,094 | 7/1982 | Elahi | 422/57 |
| 4,373,812 | 2/1983 | Stein et al. | 422/72 |

Primary Examiner—Gary P. Straub
Attorney, Agent, or Firm—Sigalos, Levine & Montgomery

[57] ABSTRACT

A rotary fluid manipulator utilizable as a diagnostic device includes a porous body having fluid passages defined therein by fluid blocking means in the porosities of the body such as openings or slots in the body or compaction of areas of the porous body to define fluid passages therebetween. Various substances or binding partners such as receptors, immunoassay or other assay test materials and test specimens can be deposited on the porous body to permit various types of test to be made by rotation of the manipulator to cause conjunctive centrifugal and wicking induced flow of fluids deposited thereupon.

13 Claims, 2 Drawing Sheets

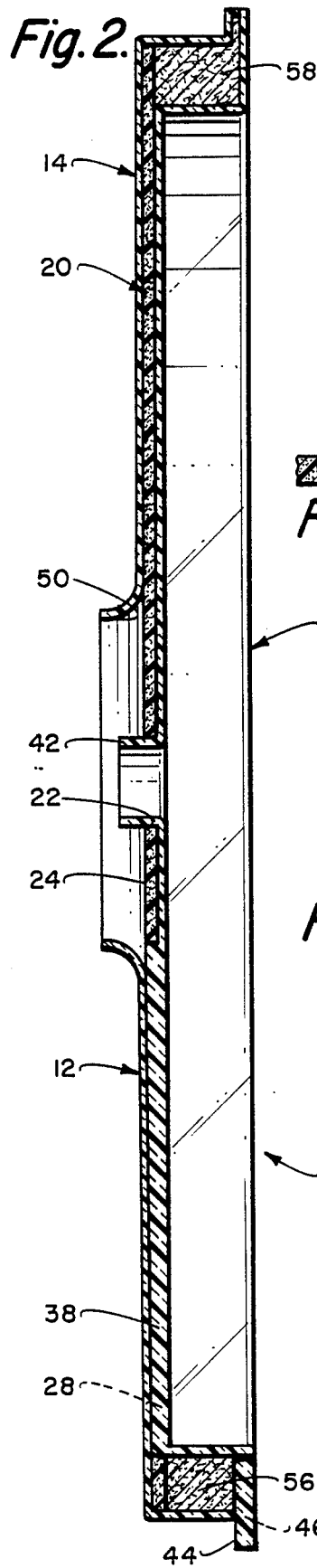
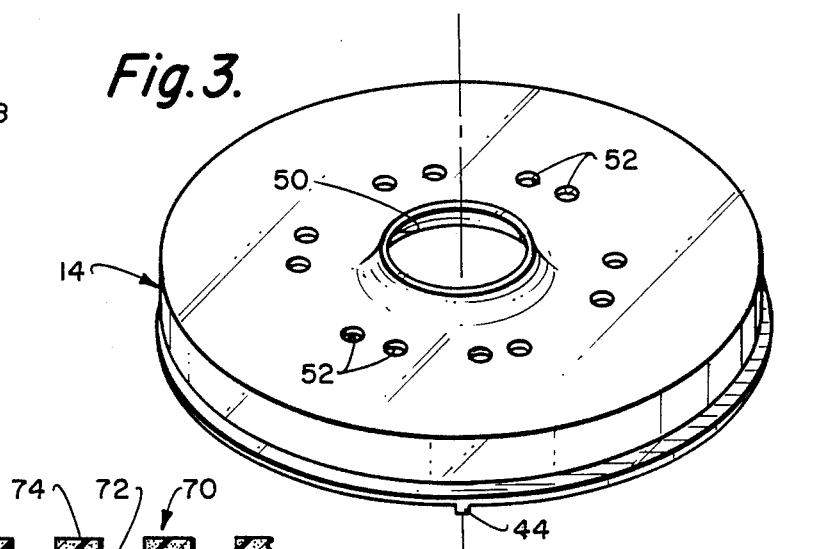
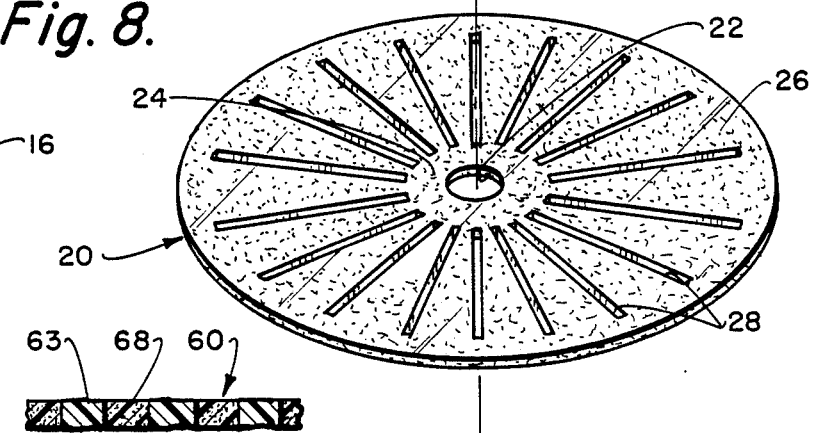
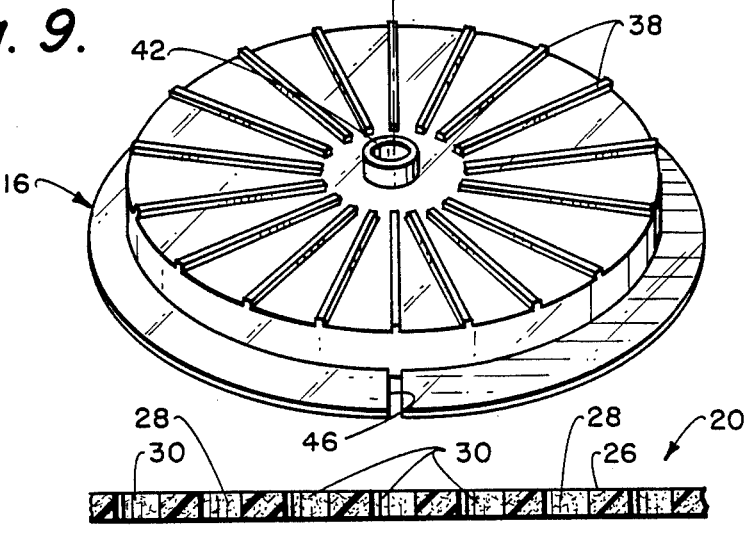
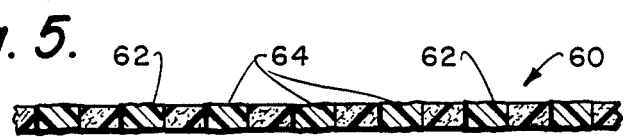

ROTARY FLUID MANIPULATOR

This application is a continuation of application Ser. No. 338,123, filed Jan. 8, 1982 now abandoned.

BACKGROUND OF THE INVENTION

Rotary diagnostic devices well known in the art are exemplified in U.S. Pat. Nos. 3,679,367, 3,744,975, 4,123,173, 4,244,916, 4,225,558, and 4,237,234.

As can be readily determined from a review of the patents cited hereinabove, prior art rotary diagnostic devices are usually fabricated by injection molding or other analagous techniques from thermosetting or thermoplastic resins and include a plurality of chambers, passages, cuvettes and the like.

Because of their relative complexity, the prior art devices entail the utilization of expensive molds and tools and are also relatively complex in construction and mode of operation.

Furthermore, because of the inherent limitations of such manufacturing techniques as injection molding, the fluid passages, chambers, cuvettes, and the like provided in prior art devices must necessarily be limited in configuration and disposition within the bodies of such prior art devices.

Moreover, since the prior art devices are relatively expensive to fabricate, the cost thereof materially reduces their availability in such markets as third world nations and the like.

OBJECTS AND ADVANTAGES OF THE INVENTION

It is, therefore, an object of our invention to provide a rotary fluid manipulator or diagnostic device which is characterized by the fact that it is fabricated from a sheet of porous material having top and bottom, generally parallel flat surfaces and characterized by the fact that the body of the manipulator or device incorporates porosities exerting a wicking action upon fluids or fluid suspended substances deposited on the body.

The body of the manipulator or device incorporates a plurality of fluid passages which are formed therein by occluding selected areas of the body to define the passages and prevent fluid flow in the occluded areas.

It is also within the scope of our invention to provide a manipulator or device characterized by the incorporation of fluid control means associated with the aforesaid fluid passages so that such characteristics as restrictions of fluid flow, adequate fluid distribution or equality or inequality of fluid distribution, among others, may be achieved. The fluid control means are provided by the same manufacturing techniques as the fluid passages, namely, the occluding of various areas of the body of the manipulator or device to accomplish the desired fluid control.

Among the techniques utilized to define the fluid passages in the body are the formation of openings such as slots, holes or other apertures to restrict fluid flow to areas of the body between said slots, holes or other apertures.

A corresponding occlusive technique includes the definition of fluid passages by the impregnation of the body in a desired fluid passage pattern with occluding materials such as thermoplastic or thermosetting resins, hot melt glue, siliconizing agents, or the like.

Another method of forming or defining fluid passageways in the body is the compaction of areas of the body by the application of pressure thereto to collapse the porosities of the body and thus define fluid passages intermediate collapsed areas.

Similarly, the fluid control means associated with the individual fluid passages can be fabricated in the same manner as the fluid passages, that is, by the formation of various shapes of apertures, the use of occlusive materials, or the compacting of selected areas of the body in association with the fluid passages.

Another object of our invention is the provision of a device of the aforementioned character which is fabricated from a sheet of fibrous material chosen generally from organic and inorganic fibers which can be readily utilized to provide porosities and associated liquid wicking of liquids deposited thereupon. Exemplary of inorganic fibers are glass fibers and exemplary of organic fibers are the various cellulose materials such as wood, paper and linen fibers.

Because such fibrous materials are relatively inexpensive and do not entail the use of expensive tools or molds to fabricate the body and its associated fluid passages and the fluid control means for such passages, the device of the invention can be produced at a cost far below the cost of the prior art devices adverted to hereinabove.

Although it is conceivable that the diagnostic device be provided in the form of a rotary body having predetermined fluid passages and fluid control means fabricated therein it is contemplated that in at least one form of the device the body will be incorporated in a housing fabricated from thermoplastic or thermosetting resins and including various ports to facilitate the deposition of test specimens or the like on the surface of the body of the device. It is also contemplated that the housing include a port or ports for the deposition of eluant thereupon and that, further, it incorporate the means for the reception of excess quantities of eluant after the eluant has functioned in operative relation with the body of the device.

Another object of our invention is the provision of a device of the aforementioned character which can be dosed with various types of reagents such as binding partners, radioisotopically treated bodies, antibodies, antigens and the like to facilitate the utilization of the device in making various types of immunoassay and other assays for diagnostic purposes.

Illustrative of such diagnostic utilization of the device is the dosing of the body with binding partners including a radioisotope labeled antigen, an antibody and, if desired, a standard or reference specimen. A test specimen is deposited on the body and a subsequently deposited eluant causes the specimen to be carried in conjunction with the radioisotope treated antigens into linking relationship with the antibody.

It will be obvious to those skilled in the art that the device of the invention can be utilized in making a wide variety of tests, analyses and the like such as radioimmunoassays, fluorescent immunoassays, enzyme immunoassays and the like.

Another object of our invention is the provision of a device of the aforementioned character which can be utilized with a wide variety of binding partners including, but not limited to, such partners as antigens and corresponding antibodies, antigens which have been radioisotopically labeled, antigens which are subjected to fluorescent or enzyme labeling and especially prepared antibodies of the character disclosed in our copending application Ser. No. 139,770 A RAPID RADI- OIMMUNOASSAY PRODUCT AND METHOD OF MAKING AND USING SAME now U.S. Pat. No. 4,399,299 issued Aug. 16, 1983.

Another object of our invention is the provision of a method of manufacturing the aforesaid device which includes the steps of fabricating the body of the device from a selected one of the aforementioned materials, for instance, glass fiber filter material. Additional steps include the dosing of the body on the perimeter with a selected binding partner, such as an antibody. Subsequently, a labeled antigen, such as a radioisotope labeled antigen is located on the body in a position in which it can be carried by an eluant into contact with the aforementioned antibody.

An additional object of our invention is the provision of a method of utilizing the aforementioned device having a plurality of binding partners thereupon, with one of the binding partners being labeled, wherein a test specimen is deposited upon the treated binding partner and an eluant is deposited on the device to carry the treated and test antigens into linking engagement with the perimetrically arranged antibody induced by wicking and centrifugal forces.

Another object of our invention is a method of fabricating the aforementioned device which includes the steps of forming the body from a selected material such as glass fiber filter material, placing pre determined antibodies and antigens, or other binding partners, in predetermined locations on the body of the device, and enclosing the body of the device in a housing.

BRIEF DESCRIPTION OF THE DRAWINGS

Other objects and advantages of the invention will be apparent from the following specification and the accompanying drawings, which are for the purpose of illustration only and in which:

FIG. 2 is a transverse sectional view taken on the broken line 2—2 of FIG. 1;

FIG. 3 is an exploded view showing the various components of one embodiment of the rotary fluid manipulator;

FIG. 5 is a sectional view taken on the line 5—5 of FIG. 4;

FIG. 7 is a sectional view taken on the broken line 7—7 of FIG. 6;

FIG. 8 is a fragmentary sectional view illustrating a portion of a body of an alternative form of the rotary fluid manipulator;

FIG. 9 is a fragmentary sectional view of an alternative form of the body of the rotary fluid manipulator.

DESCRIPTION OF PREFERRED EMBODIMENTS OF THE INVENTION

Figure 1:
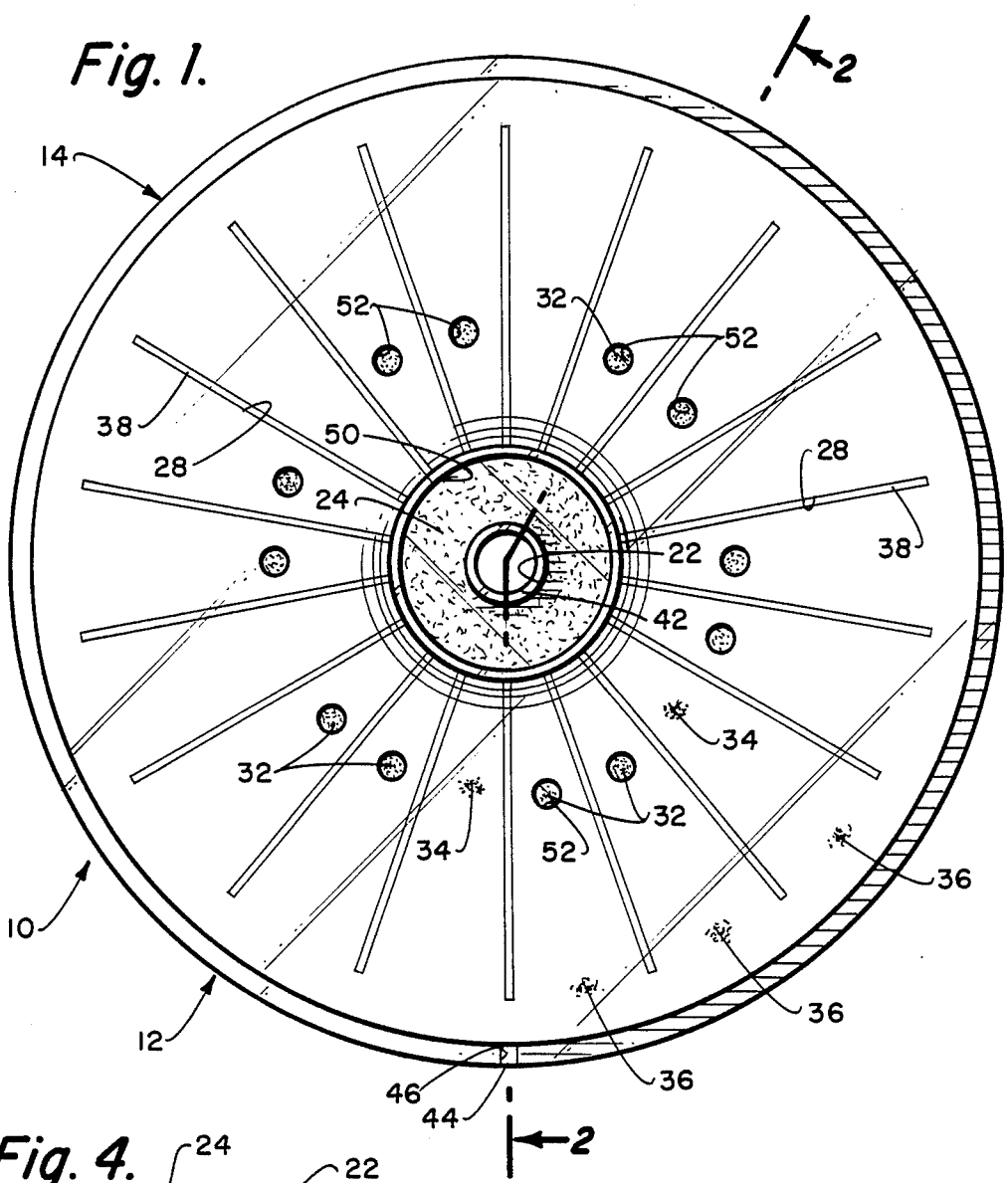
FIG. 1 is a top plan view showing the assembled rotary fluid manipulator.

Referring to the drawings, and particularly to FIGS. 1-5 thereof, we show a rotary fluid manipulator 10 which is characterized by the utilization of a two part housing 12 consisting of an upper portion 14 and a lower portion 16, FIG. 2. The housing 12 may be fabricated from any one of a variety of materials, but in the present embodiment of the invention, is formed from a transparent synthetic resin such as an acrylic resin and is fabricated by injection molding of the upper and lower portions 14 and 16 thereof.

Of course, it will be obvious to those skilled in the art that there are innumerable ways in which the housing can be fabricated including such expedients as blow molding, vacuum forming and the like. In addition, a wide variety of material is available for utilization in fabricating the housing.

Figure 4:
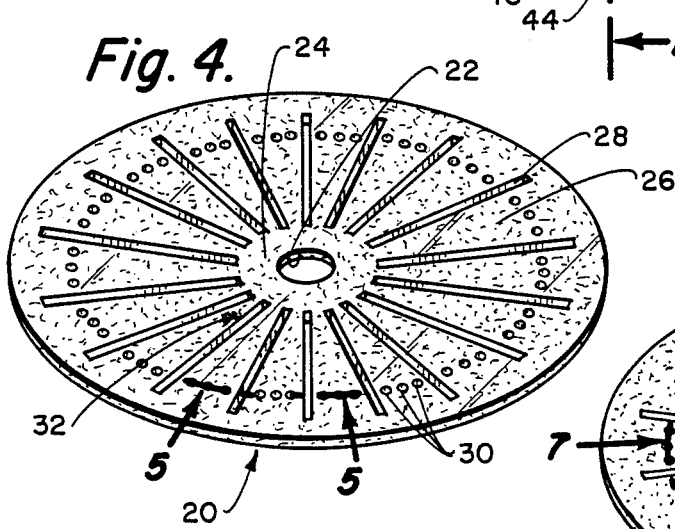
FIG. 4 is an isometric view illustrating the manipulator body.

Enclosed within the housing is the body 20 of the fluid manipulator, FIG. 4, which is fabricated in a disc configuration from a material characterized generally by the incorporation of porosities which induce a wicking action on fluid deposited on the central portion of the body. Although we disclose the preferred embodiments of the invention as incorporating a body having a circular configuration, it is contemplated that various alternative configurations may be utilized, if desired, such as a truncated cone, a truncated pyramidal structure and the like.

We have ascertained that a highly effective material for utilization in fabricating the body 20 is a filter material manufactured from compacted glass fibers. This material is susceptible to the various manufacturing steps encompassed in the fabrication of the various forms of the body and is also inherently mechanically stable and relatively easy to handle during the manufacturing process. There are other porous and fibrous materials which can be utilized in substitution for the compacted glass fiber material referred to hereinabove. Included among these materials are cellulosic materials such as filter materials formed from compacted paper or linen or other cloth fibers. It is also conceivable that ceramic and synthetic materials incorporating interconnected porosities might be utilized so long as these materials would provide the requisite wicking action and be relatively easily fabricated during the manufacturing process of the body.

The rotary fluid manipulator 10 is designed to be utilized, as mentioned above, in a variety of assays including radioimmunoassays, enzyme immunoassays and fluorescent immunoassays. It is also designed to be utilized with the rotary table similar to those utilized in the well known laboratory centrifuge so that the eluant deposited upon the body may be caused to flow outwardly towards the perimeter thereof by centrifugal and wicking forces to act as a suspensory and carrying agent for the various reagents deposited on the body during the manufacturing process and subsequently deposited upon the body as specimens to be subjected to the desired assay.

Formed in the center of the body 20 is a circular opening 22 adapted to receive the mounting stud of a rotary table, not shown. Immediately adjacent the centrally located opening is an eluant receiving area 24 which is adapted to receive eluant deposited upon the area in a manner to be described in greater detail below. In making the assay, it is desirable that as many individual assays and standard assays be made as is feasibly possible by the utilization of a single rotary fluid manipulator for the various purposes of economy, machine time and speed in making the assays.

Therefore, the body is divided into a plurality of sections 26 so that a separate assay or a corresponding standard assay may be accomplished by the utilization of each of the separate sections. Defining the sections 26 are fluid blocking means constituted by radial slots 28 said fluid blocking means being so arranged that the slots 28 defining the same initiate adjacent the eluant receiving area 24 and terminate inwardly of the perimeter of the body 20. Although a plurality of radial slots 28 are shown as defining the fluid blocking means, it is within the contemplation of our invention that various types of slots or openings be utilized to block the flow of fluid through the porosities of the fibrous disc constituting the body 20 and the relatively simple radial slots are utilized for the purpose of illustration only.

Located outwardly of the center of the body 20 but a substantial distance inwardly of the perimeter thereof are fluid control means constituted by a plurality of orifices 30 punched or otherwise formed through the fibrous material of the body 20. The fluid control means constituted by the orifices 30 serve as restrictions to cause the eluant flow to be evenly distributed across the respective section or segment of the body to insure the proper functioning of the body in the conduct of the assay, in a manner that will be described in greater detail below.

Although the fluid control means are supplied in the form of orifices 30 it will be obvious to those skilled in the art that the number and configuration of the orifices can be altered without materially diverging from the teachings of the present invention.

For instance, instead of a plurality of orifices one large orifice may be utilized. Instead of circular orifices square orifices or elongated slots may be punched through the body.

It is intended that the rotary fluid manipulator of the present invention be utilized, as mentioned hereinabove, in the laboratory as a means of making a variety of assays on specimens derived from various organisms, but, particularly, the human organism.

To facilitate the utilization of the rotary fluid manipulator in this manner, the body 20 is subjected to the deposition of various binding partners thereupon which will permit the attainment of the desired assay on the subject specimen.

For instance, during the manufacturing process labeled antigens indicated generally at 32 may be deposited on the body with a standard control 34 deposited on the respective section or segment 26.

Outwardly of the fluid control means and adjacent the perimeter of the body 20 are deposited antibodies 36, the labeled antigens and the antibodies being binding partners whose interaction will result in the desired assay accomplishment.

Of course, the antigens 32 deposited on the body 20 are labeled antigens and are critical elements in the performance of the respective assay. They may be labeled by isotopic, enzyme or fluorescent labels since the basic wicking and centrifugal action which takes place during the performance of the assay is susceptible of any one of the labeling techniques. Of course, it is not intended that the labeling be limited to the aforementioned since it is obvious that other utilizations of the body would not affect the inherent characteristics thereof.

It is contemplated that the slots 28 constituting the fluid blocking means, the orifices 30 constituting the fluid control means and the centrally located opening 22 together with the circular configuration of the body 20 be attained by a variety of means including the utilization of cutting dies which cut and punch the material from the slots and openings while cutting the circular shape of the body 20 from a web of the material.

After the mechanical fabrication of the body 20 and the deposition of the first and second binding partners thereupon as constituted by the labeled antigens and the selected antibodies, the body 20 is placed in the housing 12 by positioning the slots 28 in the body 20 over corresponding locating ribs 38 formed in the lower portion 16 of the housing 12.

A centrally located boss 42 provided on the lower portion 16 of the housing 12 is received in the corresponding opening 22 of the body 20. The upper portion 14 of the body 12 is then superimposed on the lower portion 16 thereof and corresponding alignment slots and bosses 44 and 46, respectively, in the upper and lower portions assist in the mating of the two components of the housing 12.

The two components 14 and 16 of the housing 12 may be permanently secured to each other by the utilization of any suitable adhesive and it is also contemplated that a mechanical interlock may be utilized in substitution therefore.

Formed in the upper portion 14 of the body 12 is an enlarged central aperture 50 which serves as the eluant dosing aperture to permit eluant to be fed to the centrally located eluant receiving area 24 of the body 20. Concentrically arranged outwardly of the eluant dosing aperture 50 is a plurality of specimen dosing orifices 52 which permit specimens to be applied to the sections incorporating the labeled antigens. It will be noted that no apertures are provided in overlying relationship with the sections 26 of the body bearing the standards.

It will be noted that a circumferential collection chamber 56 is provided at the perimeter of the body to collect excess fluid resulting from the centrifugal and wicking actions to which the eluant is subjected and that chamber may incorporate a suitable absorbent material 58, such as a cellulosic absorbent or the like.

Before or after the fluid manipulator 10 is placed upon a rotary table, the specimens can be manually or automatically deposited upon the diagnostic sections 26 through the dosing orifices 52. Correspondingly, the eluant is deposited through the eluant dosing aperture 50 on the eluant receiving area 24 and the rotary table is activated to cause the eluant to be subjected to centrifugal action. As the eluant moves outwardly from the centrally located eluant receiving area 24, it is channeled between the fluid blocking means constituted by the slots 28 and initially engages the first binding partner constituted by the labeled antigen and the specimen or standard in each of the diagnostic sections. Continued centrifugal and wicking action of the rotary fluid manipulator 10 causes continued outward flow of the eluant bearing the labeled antigen and specimen through the restrictions constituted by the fluid control orifices 30 and subsequent impingement of the eluant, antigen, specimen composite on the antibodies 36.

When this occurs the labeled antigen and antibodies bind and the rotary fluid manipulator is subjected to a measurement which may be accomplished by a measurement device specifically designed for the particular type of label utilized. For instance, in a radioimmunoassay, a gamma ray counter may be utilized. In enzyme and fluorescent label assays, various types of light sources, filters and photo detectors may be utilized in the measurement process.

Figure 6:
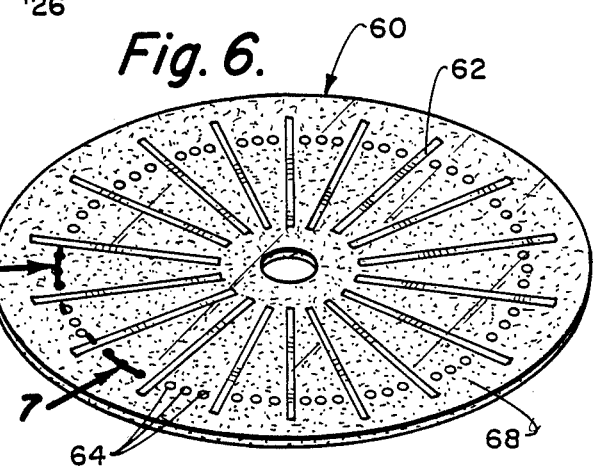
FIG. 6 is an isometric view of another embodiment of the body of the rotary fluid manipulator.

Other means of fabricating the body of the fluid manipulator may be utilized to create the fluid blocking means and the fluid control means. For instance, the body 60, FIG. 6, has fluid control means 62 constituted by fluid impervious radial sections of the body which have been impregnated with a variety of occlusive substances such as synthetic plastic impregnants, synthetic glues or the like. This is also true of the fluid blocking means 64 which are constituted by similar plastic impregnants or the equivalent.

In the process of forming and manufacturing the body 60, the impregnants are deposited in the fibrous porosities of the body by the utilization of devices such as silk screens, or the like. Since no openings or slots are formed in the body the need for locating ribs 38 is eliminated and loading pins, not shown, may be used instead.

An alternative method of creating fluid blocking and control means is illustrated schematically in the fragmentary view of FIG. 8 wherein the body 70 has compacted radial areas 72 corresponding to the configuration of the radial slots 28 of the body 20 which constitute fluid blocking means causing fluid to flow in the areas 74 which are the diagnostic sections of the body 70. Similar compacting techniques can be utilized to form the fluid control means which are provided by the apertures 30 in the body 20. The compaction of the material of the body 70 to provide the fluid blocking and control means can be accomplished by the utilization of a die having the requisite pattern of fluid blocking and control means provided thereupon. The impingement of the die under pressure on upper surface of the body 70 will cause the suitable deformation and compaction of the body to collapse the porosities in the designated areas and achieve the proper fluid flow to the perimeter of the body 70 in the manner described in outlining the mode of utilization and operation of the body 20 of the first embodiment of the invention.

Shown schematically in FIG. 9 of the drawings is the manner in which radial areas 63 of the body 60 can be impregnated to define separate diagnostic sections 68.

It will be obvious to those skilled in the art that we provide by our invention a rotary diagnostic device which is characterized by simplicity of manufacture and ease of utilization. Although we disclose the utilization of a housing 12 to encompass the respective bodies of the device, it is not necessary that such a housing be provided since it is conceivable that the rotary table be provided with encapsulating means capable of receiving the body itself absent the presence of the housing shown and disclosed hereinabove.

Moreover, it is not intended that the utilization of the rotary fluid manipulator be limited to any particular type of assays since it will be obvious to those skilled in the art that a wide variety of applications of the rotary fluid manipulator can be found in making various types of assays. Because of its relatively low cost of manufacture and ease of utilization, it provides a marked advance over the prior art and it is not intended that the disclosure thereof presented hereinabove be taken in a limiting connotation but that the scope of the invention be defined by the following claims.

We claim:

1. In a diagnostic device for fluid specimens, the combination of; a housing, a bibulous porous body in said housing incorporating irregular interstices which impart wicking characteristics to said body, at least one aperture in the interior of said housing for applying fluids to said body, a plurality of fluid passage sections defined in said body by occluding means which prevent fluid flow beyond the edges of said passage sections defined by said occluding means; and absorbent means removed from said at least one aperture at an end of said fluid passage sections and in contact therewith for common collection of excess fluids from said fluid passage sections.

2. The device of claim 1 in which said occluding means are slots in said body.

3. The diagnostic device of claim 1 or 2 wherein each of said fluid passage sections has at least one antibody or antigen thereon situated between said at least one aperture and said absorbent means.

4. In a diagnostic device for fluid specimens, the combination of: a housing, a bibulous porous body in said housing incorporating irregular interstices imparting wicking characteristics to said body; a plurality of fluid passage sections within said body defined by occluding means which prevent fluid flow beyond the edges of said passage sections defined by said occluding means; and absorbent means at an outside edge of said fluid passage sections in contact with said body for common collection of excess fluids from each of said fluid passage sections; said housing having eluant receiving means and specimen receiving means in the interior thereof to permit eluant to be fed onto said body and fluid specimen to be deposited on said body to subject said eluant and specimen to wicking action in said body through said fluid passage sections.

5. The device of claim 4 in which said housing includes upper and lower walls, said walls being joined by a perimetrical edge and said body is sandwiched between said upper and lower walls.

6. The diagnostic device of claim 4 or 5 wherein each of said fluid passage sections has at least one antibody or antigen thereon situated between said eluant receiving means and said absorbent means.

7. In a diagnostic device for fluid specimens, the combination of: a housing having upper and lower walls and a perimetrical edge defining a receptacle therebetween, said housing having fluid access means in the interior of said upper wall; a bibulous porous body located in said receptacle adjacent said access means, said body having irregular interstices imparting wicking characteristics to said body and having a plurality of fluid flow passage section defined therein by occluding means preventing fluid flow beyond the edges of said passage sections formed upon said body through said access means is channeled through said passage sections; and absorbent reservoir means at said perimental edge of said fluid passage sections in contact with said body for common collection of excess fluids from each of said fluid passage sections.

8. The device of claim 7 in which said access means is constituted by eluant and specimen receiving openings therein for, respectively, dosing said body with eluant and applying specimen to said body.

9. The diagnostic device of claim 7 or 8 wherein each of said fluid passage sections has at least one antibody or antigen thereon situated between said fluid access means and said absorbent means.

10. The diagnostic device of any one of claims 1 or 4 to 8 wherein said occluding means is a fluid impervious substance.

11. The diagnostic device of any one of claims 1, 2 or 4 to 8 wherein said fluid passage sections extend radially from the center of said bibulous porous body.

12. A diagnostic device for fluid specimens comprising a housing having upper and lower wall means defining a chamber therebetween, an eluant receiving opening and a specimen receiving opening in the interior of the upper wall of said housing, a bibulous porous body in said chamber having wicking characteristics, a plurality of fluid passage sections in said body separated from each other by a fluid impervious substance which prevents fluid flow beyond the edges of said fluid passage sections defined by said fluid impervious substnace, and absorbent means at an outside end of said fluid passage sections in contact with said body for common collection of excess fluids from said fluid passage sections.

13. The diagnostic device of claim 12 wherein each of said fluid passage sections has an antibody or antigen thereon situated between said eluant opening and said absorbent means.

* * * * *

UNITED STATES PATENT AND TRADEMARK OFFICE
CERTIFICATE OF CORRECTION

PATENT NO. : 4,938,927
DATED : July 3, 1990
INVENTOR(S) : Kelton, et al

It is certified that error appears in the above-identified patent and that said Letters Patent is hereby corrected as shown below:

Column 8, line 43, after the word "formed" insert the phrase -- by said occluding means such that fluid deposited --.

Signed and Sealed this

Twenty-eighth Day of January, 1992

Attest:

HARRY F. MANBECK, JR.

*Attesting Officer*     *Commissioner of Patents and Trademarks*